(12) United States Patent
Lenz et al.

(10) Patent No.: US 8,216,781 B2
(45) Date of Patent: Jul. 10, 2012

(54) GENE POLYMORPHISMS AS PREDICTORS OF TUMOR PROGRESSION AND THEIR USE IN CANCER THERAPY

(75) Inventors: Heinz-Josef Lenz, Los Angeles, CA (US); Wu Zhang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 103 days.

(21) Appl. No.: 12/523,521

(22) PCT Filed: Jan. 17, 2008

(86) PCT No.: PCT/US2008/000651
§ 371 (c)(1), (2), (4) Date: Aug. 10, 2009

(87) PCT Pub. No.: WO2008/088855
PCT Pub. Date: Jul. 24, 2008

(65) Prior Publication Data
US 2010/0113459 A1 May 6, 2010

Related U.S. Application Data

(60) Provisional application No. 60/885,610, filed on Jan. 18, 2007.

(51) Int. Cl.
*C12Q 1/68* (2006.01)
(52) U.S. Cl. .................................................. 435/6
(58) Field of Classification Search .................. None
See application file for complete search history.

(56) References Cited

U.S. PATENT DOCUMENTS

| 2006/0094012 A1* | 5/2006 | Lenz et al. ................ 435/6 |
| 2006/0115827 A1* | 6/2006 | Lenz ........................ 435/6 |
| 2007/0207486 A1 | 9/2007 | Lenz |

FOREIGN PATENT DOCUMENTS

| WO | WO 2007/103814 | 9/2007 |
| WO | WO 2007/103823 A2 | 9/2007 |
| WO | WO 2008/088854 | 7/2008 |
| WO | WO 2008/088855 | 7/2008 |
| WO | WO 2008/088860 | 7/2008 |
| WO | WO 2008/088861 | 7/2008 |
| WO | WO 2008/088893 | 7/2008 |
| WO | WO 2008/089465 | 7/2008 |
| WO | WO 2009/140556 | 11/2009 |
| WO | WO 2010/124264 A2 | 10/2010 |
| WO | WO 2010/124265 A1 | 10/2010 |

OTHER PUBLICATIONS

Zhang et al (Clinical Colorectal Cancer, Jul. 2005, 5:124-131, IDS).*
Allen et al. (2006) "Predicting the outcome of chemotherapy for colorectal cancer," Cur Opinion Pharmacol 6:332-6.
Fox et al. (1998) "Angiogenesis in normal tissue adjacent to colon cancer," *J. Surg. Oncol.* 69(4):230-4.
Kuniyasu et al. (2000) "Induction of angiogenesis by hyperplastic colonic mucosa adjacent to colon cancer," *Am. J. Pathol.* 157(5):1523-35.
Lenz et al. (2006) "EGFR-targeted therapies in solid tumors," www.CancerPublications.com, 38 pages.
Liotta at al. (2001) "The microenvironment of the tumour-host interface," *Nature* 411(6835):375-9.
Loktionov (2004) "Common gene polymorphisms, cancer progression and prognosis," Cancer Lett. 208(1):1-33.
Lurje et al. (2008) "Polymorphisms in VEGF and IL-8 predict tumor recurrence in stage III colon cancer," Annal of Oncol 19:1734-41.
Lurje et al. (2010) "Genetic variations in angiogenesis pathway genes associated with clinical outcome in localized gastric adenocarcinoma," Annal of Oncol 21(1):78-86.
Manegold et al. (2008) "ICAM-1, GRP-78, and NFkB gene polymorphisms and clinical outcome in patients (pts) with metastatic colorectal cacner (mCRC) treated with first line 5-FU or capecitabine in cominbation with oxaliplatin and bevacizumab (FOLFOX/BV or XELOX/BV)," Journal of Clinical Oncology, 2008 ASCO Annual Meeting Proceedings (Post-Meeting Edition) 26(15S) (May 20 Supplement) 2008:4134.
Ning et al. (2009) "VEGF and VEGFR1 gene expression levels and tumor recurrence in adjuvant colon cancer," J Clin Oncol. ASCO Annual Meeting 2009, 27(15S):4040.
Pander et al. (2007) "Pharmacogenetics of EGFR and VEGF inhibition," *Drug Discov. Today* 12(23-24):1054-60.
Shaye et al. (2007) "Polymorphisms in angiogenesis related genes predict clinical outcome in patients (pts) with metastatic colorectal cancer (mCRC) treated with first line 5-FU or capecitabine in combination with oxaliplatin and bevacizumab (FOLFOX/BV or XELOX/BV)," Journal of Clinical Oncology, 2007 ASCO Annual Meeting Proceedings Part I. 25(18S) (Jun. 20 Supplement), 2007: 10576.
Smith, et al. "Cytokine gene polymorphisms and breast cancer susceptibility and prognosis." European Journal of Immunogenetics: Official Journal of the British Society for Histocompatibility and Immunogenetics 31(4):167-73.
Vallbohmer et al. (2006) "Molecular determinants of irinotecan efficacy," Int J Cancer 119:2435-42.
Vallböhmer et al. (2005) "Molecular determinants of cetuximab efficacy," *J. Clin. Oncol* 23(15):3536-44.
Yan and Beckman (2005) "Pharmacogenetics and pharmacogenomics in oncology therapeutic antibody development," Biotechniques 39:565-8.
Zhang et al. (2009) "Genetic variants in angiogenesis pathway associated with clinical outcome in NSCLC patients (pts) treated with bevacizumab in combination with carboplatin and paclitaxel: Subset pharmacogenetic anaysis of ECOG 4599," J Clin Oncol 27(15S):8032.

(Continued)

*Primary Examiner* — Laura B Goddard
(74) *Attorney, Agent, or Firm* — Foley & Lardner LLP; Antoinette F. Konski; Alex Y. Nie

(57) ABSTRACT

The invention provides compositions and methods for determining the likelihood of successful treatment with a pyrimidine based antimetabolite chemotherapy drug and a platinum based chemotherapy drug, such as 5-FU/oxaliplatin. The methods comprise determining the genomic polymorphism present in a predetermined region of a gene of interest and correlating the polymorphism to the predictive response. Patients identified as responsive are then treated with the appropriate therapy.

25 Claims, 3 Drawing Sheets

OTHER PUBLICATIONS

Zhang et al. (2005) "Gene polymorphisms of epidermal growth factor receptor and its downstream effector, interleukin-8, predict oxaliplatin efficacy in patients with advanced colorectal cancer," *Clin. Colorectal Cancer* 5(2):124-31.

Zhang et al. (2005) "Association between dinucleotide repeat (CA) polymorphism of nuclear factor kappa-beat (NF-KB) and local recurrence of stage II/III rectal cancer patients treated with chemoradiation," Int J Radiation: Oncol Biol Phys 60(1):S423.

Zhang et al. (2006) "Cyclin D1 and epidermal growth factor polymorphisms associated with survival in patients with advanced colorectal cancer treated with Cetuximab," Pharmacogenetics Genomics 16:475-83.

Lurje, G. et al. (2008) "Polymorphisms in *Cyclooxygenase-2* and *Epidermal Growth Factor Receptor* Are Associated with Progression-Free Survival Independent of K-ras in Metastatic Colorectal Cancer Patients Treated with Single-Agent Cetuximab," Clin Cancer Res 14(23): 7884-7895.

Renzoni, E. et al. (Jul. 2000) "Distribution of Novel Polymorphisms of the Interleukin-8 and CXC Receptor 1 and 2 Genes in Systemic Sclerosis and Cryptogenic Fibrosing Alveolitis," Arthritis & Rheumatism 43(7): 1633-1640.

\* cited by examiner

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ttgttctaac acctgccact ct    22

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcaaacctg agtcatcaca                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catctttgct gtcgtcctca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcacaggtc tcctggatca                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtaaaccat ggtctgtacc                                              20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacaaaatgt tgaatgagtg gg                                           22
```

GENE POLYMORPHISMS AS PREDICTORS OF TUMOR PROGRESSION AND THEIR USE IN CANCER THERAPY

CROSS-REFERENCE TO RELATED APPLICATION

This application is a national stage application under 35 U.S.C. §371 of International Application No. PCT/US2008/000651, filed Jan. 17, 2008, which in turn claims the benefit under 35 U.S.C. §119(e) of provisional application U.S. Ser. No. 60/885,610, filed on Jan. 18, 2007, the contents of each of which are incorporated by reference into the present disclosure in their entireties.

FIELD OF THE INVENTION

This invention relates to the field of pharmacogenomics and specifically to the application of genetic polymorphism(s) to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Pharmacogenetics and pharmacogenomics are multidisciplinary research efforts to study the relationship between genotype, gene expression profiles, and phenotype, as expressed in variability between individuals in response to or toxicity from drugs. Indeed, it is now known that cancer chemotherapy is limited by the predisposition of specific populations to drug toxicity or poor drug response. For a review of the use of germline polymorphisms in clinical oncology, see Lenz, H.-J. (2004) J. Clin. Oncol. 22(13):2519-2521; Park, D. J. et al. (2006) Curr. Opin. Pharma. 6(4):337-344; Zhang, W. et al. (2006) Pharma. and Genomics 16(7):475-483 and U.S. Patent Publ. No. 2006/0115827. For a review of pharmacogenetics and pharmacogenomics in therapeutic antibody development for the treatment of cancer, see Yan and Beckman (2005) Biotechniques 39:565-568.

Colorectal cancer (CRC) represents the second leading lethal malignancy in the USA. In 2005, an estimated 145,290 new cases will be diagnosed and 56,290 deaths will occur. Jemal, A. et al. (2005) Cancer J. Clin. 55:10-30. Despite advances in the treatment of colorectal cancer, the five year survival rate for metastatic colon cancer is still low, with a median survival of 18-21 months. Douglass, H. O. et al. (1986) N. Eng. J. Med. 315:1294-1295.

The Food and Drug Administration has approved the use of Cetuximab, an antibody to the epidermal growth factor receptor (EGFR), either alone or in combination with irinotecan (also known as CPT-11 or Camptosar®) to treat patients with EGFR-expressing, metastatic CRC, who are either refractory or intolerant to irinotecan-based chemotherapy. One recent study (Zhang, W. et al. (2006) Pharmacogenetics and Genomics 16:475-483) investigated whether polymorphisms in genes of the EGFR signaling pathway are associated with clinical outcome in CRC patients treated with single-agent Cetuximab. The study reported that the cyclin D1 (CCND1) A870G and the EGF A61G polymorphisms may be useful molecular markers for predicting clinical outcome in CRC patients treated with Cetuximab.

Other polymorphisms have been reported to associated with clinical outcome. Twenty-one (21) polymorphisms in 18 genes involved in the critical pathways of cancer progression (i.e., drug metabolism, tumor microenvironment, cell cycle regulation, and DNA repair) were investigated to determine if they will predict the risk of tumor recurrence in rectal cancer patients treated with chemoradiation. Gordon, M. A. et al. (2006) Pharmacogenomics 7(1):67-88. However, to the best of Applicant's knowledge, correlation of the polymorphisms identified herein and responsiveness to 5-fluorouracil (5-FU)/oxaliplatin therapy has not been previously reported.

DESCRIPTION OF THE EMBODIMENTS

This invention provides methods to identify patients likely to respond to a selected therapy and to select the appropriate therapy for patients suffering from a gastrointestinal malignant, metastatic or non-metastatic tumor or cancer, wherein the appropriate therapy comprises administration of an effective amount of a pyrimidine based antimetabolite chemotherapy drug and a platinum based chemotherapy drug. In one aspect, these drugs are 5-fluorouracil and/or oxaliplatin or an equivalent of each thereof. The method requires detecting the identity of at least one allelic variant of a predetermined gene selected from the group identified in the left hand column of Table 1, below.

TABLE 1

| Allele | Predictive Polymorphism | Measured Response |
|---|---|---|
| CA repeat in Intron 5 in the ER-β gene | 1 allele with <22 repeats in the ER-β gene | Tumor response and time to tumor progression |
| T251A SNP for IL-8 | A/A for the IL-8 T251 SNP | Time to tumor progression |
| A730G SNP in ER-β | G/G or A/G for the A730G SNP in ER-β | Time to tumor progression |
| C785T for CXCR2 SNP | T/T or T/C for C785T SNP for CXCR2 | Tumor response |

For patients having at least one genetic polymorphism as identified in the center column of Table 1, this invention also provides methods for treating these patients by administering an effective amount of a pyrimidine based antimetabolite chemotherapy drug and a platinum based chemotherapy drug such as 5-FU and/or oxaliplatin and equivalents of each thereof. In a further aspect, leucovorin is added to the treatment.

The various embodiments are set forth herein.

In one aspect, the invention is a method for identifying responsiveness to chemotherapy by assaying a suitable patient sample from a patient suffering from a solid malignant tumor or gastrointestinal cancer, for at least one polymorphism identified in the left hand column of Table 1, above. In a further aspect, the invention is for identifying responsiveness to chemotherapy by assaying a suitable patient sample wherein the patient is suffering from a cancer that has been treated with such therapy, e.g., gastrointestinal cancers or alternatively, ovarian cancer, head and neck cancer and advanced hepatocarcinoma. Patients having at least one, or alternatively at least two, or alternatively at least three or alternatively all four genotype(s) selected from ER-β (C/A 3'UTR or A1730G), IL-8 T-251A, or CXCR2 C785T as identified in the center column of Table 1, are likely responsive to chemotherapy comprising, or alternatively consisting essentially of, or yet further consisting of, the administration of an effective amount of a pyrimidine based antimetabolite chemotherapy drug and a platinum based chemotherapy drug such as 5-FU and/or oxaliplatin and equivalents of each thereof, wherein responsiveness is any positive clinical or sub-clinical response, such as reduction in tumor load or size, increase in time to tumor progression, increase in progression free survival or increase in overall survival. For time to tumor progression, both ER-β polymorphisms produced a positive response. For IL-8, T-251A polymorphism selects patients for 5-FU and/or oxaliplatin therapy wherein clinical response was elongation in the time to tumor progression. For tumor response, the ER-β repeat and CXCR2 C785T produced positive correlation with therapy as measured by, in one aspect, reduction in tumor load or size (tumor response).

In one aspect, the patient suitable for this method and selective for said therapy is suffering from a solid malignant tumor such as a gastrointestinal tumor, e.g., from rectal cancer, colorectal cancer, metastatic colorectal cancer, colon cancer, gastric cancer, lung cancer, non-small cell lung cancer and esophageal cancer. In an alternative aspect, the patient is suffering from colorectal cancer. In yet a further aspect, the patient is suffering from metastatic colorectal cancer. Without being bound by theory, Applicants intend that the methods are also useful to identify patients likely to respond to the combination therapy when the patient is suffering from lung cancer, ovarian cancer, head and neck cancer or hepatocarcinoma as these cancers have been successfully treated with an effective amount of a pyrimidine based antimetabolite chemotherapy drug and a platinum based chemotherapy drug such as 5-FU and/or oxaliplatin and equivalents of each thereof.

To practice this method, the sample is a patient sample containing the tumor cells, tumor tissue, normal tissue adjacent to said tumor, normal tissue distal to said tumor or peripheral blood lymphocytes. In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

These methods are not limited by the technique that is used to identify the polymorphism of interest. Suitable methods include but are not limited to the use of hybridization probes, antibodies, primers for PCR analysis and gene chips or software for high throughput analysis. Additional polymorphisms can be assayed and used as negative controls. Additional negative controls are identified in the experimental section below.

After a patient has been identified as likely responsive based on possession of one or more of the polymorphisms identified in Table 1, the method may further comprise, or alternatively, consist essentially of, or yet further consist of administering or delivering an effective amount of a pyrimidine based antimetabolite chemotherapy drug and a platinum based chemotherapy drug such as 5-FU and/or oxaliplatin and equivalents of each thereof. In a further aspect, leucovorin is added to the treatment. Methods of administration of pharmaceuticals are known in the art and briefly described herein.

In another aspect, the invention is a method for identifying and selecting a therapy comprising pyrimidine based antimetabolite chemotherapy drug and a platinum based chemotherapy drug such as 5-FU and/or oxaliplatin and equivalents of each thereof by assaying a suitable patient sample from a patient suffering from a solid malignant tumor or gastrointestinal cancer, for at least one, or alternatively at least two, or alternatively at least three, or alternatively all four polymorphisms identified in Table 1, above. Applicant has identified that polymorphisms in the genes selected from (ER-β) CA repeat 3'UTR or A1730G or (CXCR2) C785T or yet further IL-8 T-251A identify those patients more likely to respond to this chemotherapy. In one aspect, these patients likely show responsiveness to combined 5-FU/oxaliplatin therapy or an equivalent thereof, wherein responsiveness is any positive clinical or sub-clinical response, e.g., selected from the group of clinical parameters of reduction in tumor load or size, time to tumor progression, progression free survival or overall survival. Suitable patients include, but are not limited to those suffering from a solid malignant tumor such as a gastrointestinal tumor, e.g., from rectal cancer, colorectal cancer, metastatic colorectal cancer, colon cancer, gastric cancer, lung cancer, non-small cell lung cancer and esophageal cancer.

To practice this method, the sample is a patient sample containing the tumor cells, tumor tissue, normal tissue adjacent to said tumor, normal tissue distal to said tumor or peripheral blood lymphocytes. These methods are not limited by the technique that is used to identify the polymorphism of interest. Suitable methods include but are not limited to the use of hybridization probes, antibodies, primers for PCR analysis and gene chips and software for high throughput analysis. Additional polymorphisms can be assayed and used as negative controls.

In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

This invention also provides a panel, a kit, software, support or gene chip for patient sampling and performance of the methods of this invention. The kits contain gene chips, probes or primers that can be used to amplify and/or for determining the molecular structure of the polymorphisms identified in the left hand column of Table 1 above. In an alternate embodiment, the kit contains antibodies or other polypeptide binding agents that are useful to identify a polymorphism of Table 1. Instructions for using the materials to carry out the invention are further provided alone or in combination with instructions for administration of a therapy as described herein. In one embodiment, the panel of genetic markers for determining whether a patient is likely responsive to a chemotherapy regime comprising administration of a pyrimidine based antimetabolite chemotherapy drug and a platinum based chemotherapy drug, contains at least one, two, three or four of a group of primers and/or probes that identify a genetic marker from the group CA repeats of the ER-β 3'UTR; ER-β A1730G SNP; IL-8 T-251A SNP; and CXCR2 C785T SNP. Additional probes or primers may also be combined with the various combinations of probes or primers to identify the polymorphisms in Table 1.

MODES FOR CARRYING OUT THE INVENTION

Figure 1:
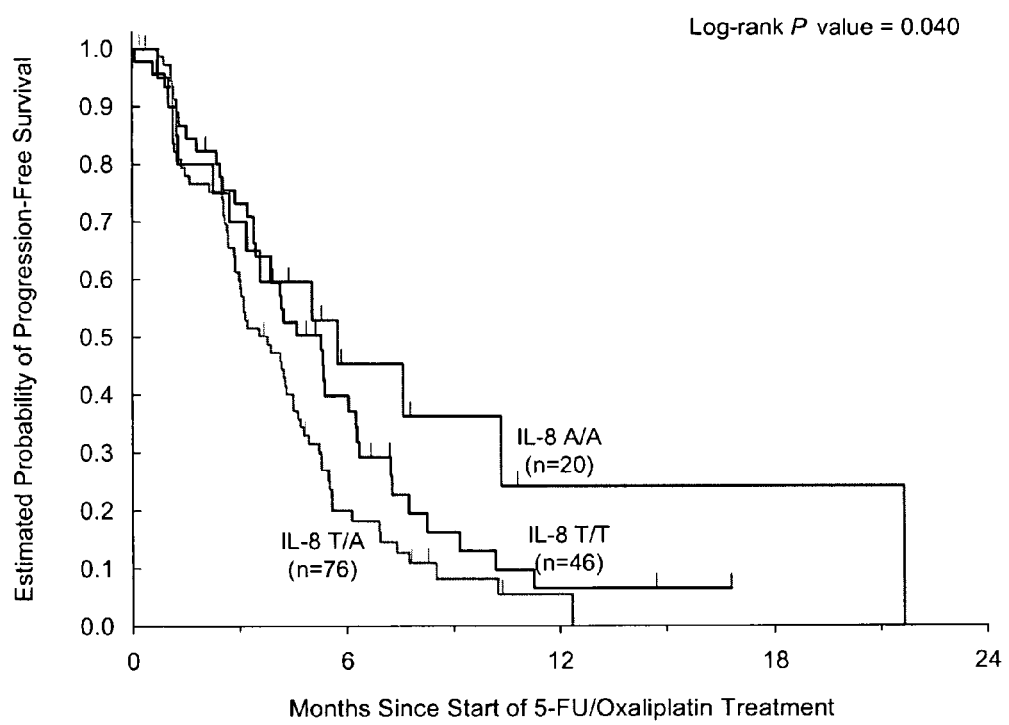
FIG. 1 graphically shows that patients possessing the A/A or T/T genotype for IL-8 gene are more responsive to disclosed therapy than those possessing T/A. It shows that progression free survival is associated with IL-8 T-251A polymorphism.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc., N.Y.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); ANIMAL CELL CULTURE (R. I. Freshney ed. (1987)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); IMMUNOCHEMICAL METHODS IN CELL AND MOLECULAR BIOLOGY (Mayer and Walker, eds., Academic Press, London (1987)); HANDBOOK OF EXPERIMENTAL IMMUNOLOGY, Volumes I-IV (D. M. Weir and C. C. Blackwell, eds. (1986)); MANIPULATING THE MOUSE EMBRYO (Cold Spring Harbor Laboratory Press, Cold Spring Harbor, N.Y. (1986)).

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively include additional steps and compositions of no significance (consisting essentially of) or alternatively, intending only the stated methods steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as X+0.1" or "X−0.1." It also is to be understood, although not always explicitly stated, that the reagents described herein are merely exemplary and that equivalents of such are known in the art.

The term "antigen" is well understood in the art and includes substances which are immunogenic. The EGFR is an example of an antigen.

A "native" or "natural" or "wild-type" antigen is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

"5-Fluorouracil" or "5-FU" is a pyrimidine analog and an antimetabolite chemotherapeutic anticancer agent. It has been in use against cancer for about 40 years, acts in several ways, but principally as a thymidylate synthase inhibitor, interrupting the action of an enzyme which is a critical factor in the synthesis of pyrimidine-which is important in DNA replication It finds use particularly in the treatment of colorectal cancer and pancreatic cancer.

Equivalents to 5-FU include prodrugs, analogs and derivative thereof such as 5'-deoxy-5-fluorouridine (doxifluoroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

"Oxaliplatin" (Eloxatin®) is a platinum-based chemotherapy drug in the same family as cisplatin and carboplatin. It is typically administered in combination with fluorouracil and leucovorin in a combination known as FOLFOX for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include without limitation cisplatin, carboplatin, aroplatin, lobaplatin, nedaplatin, and JM-216 (see McKeage et al. (1997) J. Clin. Oncol. 201:1232-1237 and in general, CHEMOTHERAPY FOR GYNECOLOGI- CAL NEOPLASM, CURRENT THERAPY AND NOVEL APPROACHES, in the Series Basic and Clinical Oncology, Angioli et al. Eds., 2004).

Leucovorin or folinic acid, is the active form of folic acid in the body. It has been used as an antidote to protect normal cells from high doses of the anticancer drug methotrexate and to increase the antitumor effects of fluorouracil (5-FU) and tegafur-uracil. It is also known as citrovorum factor and Wellcovorin. This compound has the chemical designation of L-Glutamic acid N[4[[(2-amino-5-formyl-1,4,5,6,7, 8hexahydro-4-oxo6-pteridinyl)methyl]amino]benzoyl], calcium salt (1:1).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

If an antibody is used in combination with the above-noted chemotherapy or for diagnosis or as an alternative to the chemotherapy, the antibodies can be polyclonal or monoclonal and can be isolated from any suitable biological source, e.g., murine, rat, sheep and canine. Additional sources are identified infra.

In one aspect, the "biological activity" means the ability of the antibody to selectively bind its epitope protein or fragment thereof as measured by ELISA or other suitable methods. Biologically equivalent antibodies, include but are not limited to those antibodies, peptides, antibody fragments, antibody variant, antibody derivative and antibody mimetics that bind to the same epitope as the reference antibody.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')$^2$ fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multi specific antibodies, diabodies, chimeric, recombinant and humanized.

The term "bispecific molecule" is intended to include any agent, e.g., a protein, peptide, or protein or peptide complex, which has two different binding specificities. The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by heavy chain constant region genes.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

The term "treating" as used herein is intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7): 1404-1411.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

"Stable disease" (SD) indicates that the patient is stable.

"Non-response" (NR) to a therapy defines patients whose tumor or evidence of disease has remained constant or has progressed.

"Overall Survival" (OS) intends a prolongation in life expectancy as compared to naïve or untreated individuals or patients.

The term "likely to respond" shall mean that the patient is more likely than not to exhibit at least one of the described clinical parameters or treatment responses, identified above, as compared to similarly situated patients.

When a genetic marker or polymorphism is used as a basis for selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of the genetic marker or polymorphism in a clinical setting is a clear indication that this parameter was used as a basis for initiating, continuing, adjusting and/or ceasing administration of the treatments described herein.

Descriptive Embodiments

This invention provides a method for selecting a therapeutic regimen or determining if a certain therapeutic regimen is more likely to treat a malignant condition such as cancer or is the appropriate chemotherapy for that patient than other available chemotherapies. In general, a therapy is considered to "treat" cancer if it provides one or more of the following treatment outcomes: reduce or delay recurrence of the cancer after the initial therapy; time to tumor progression (TTP), decrease in tumor load or size (tumor response or TR), increase median survival time (OS) or decrease metastases. The method is particularly suited to determining which patients will be responsive or experience a positive treatment outcome to 5-FU/oxaliplatin or an equivalent chemotherapy. These methods are useful to select therapies for highly aggressive cancers such as colorectal cancer or metastatic colon cancer.

In one embodiment, the therapy further comprises adjuvant radiation therapy or other suitable therapy, such as administration of an effective amount of leucovorin.

Thus, in one aspect, this invention is a method for determining if a human gastrointestinal cancer patient is likely responsive to a therapy comprising administration of a pyrimidine based antimetabolite chemotherapy drug and a platinum based chemotherapy drug, comprising screening a suitable cell or tissue sample isolated from said patient for at least one genetic polymorphism of the group:
  a. CA repeats of the ER-β 3'UTR;
  b. ER-β A1730G SNP;
  c. IL-8 T-251A SNP; or
  d. CXCR2 C785T SNP,
  wherein for the genetic polymorphism screened, the presence of at least one genetic polymorphism of the group:
    a. (1 allele with <22 CA repeats) of the ER-β 3'UTR;
    b. (G/G or A/G) of the ER-β A1730G SNP;
    c. (A/A) for the IL-8 T-251A SNP; or
    d. (T/T or T/C) for the CXCR2 C785T SNP,
  indicates that the patient is likely responsive to said chemotherapy.

For the practice of the method, the gastrointestinal cancer is a metastatic or non-metastatic cancer selected from the group consisting of rectal cancer, colorectal cancer, colon cancer, gastric cancer, lung cancer, non-small cell lung cancer and esophageal cancer. In one embodiment, the patient is suffering from colorectal cancer and in a further embodiment, is suffering from metastatic colorectal cancer. In a yet further aspect, the colorectal cancer is refractory to 5-fluorouracil and irinotecan based chemotherapy. Without being bound by theory, Applicants intend that the methods are also useful to identify patients likely to respond to the combination therapy when the patient is suffering from lung cancer, ovarian cancer, head and neck cancer or hepatocarcinoma as these cancers have been successfully treated with an effective amount of a pyrimidine based antimetabolite chemotherapy drug and a platinum based chemotherapy drug such as 5-FU and/or oxaliplatin and equivalents of each thereof alone or in combination with other inert carriers of no therapeutic significance to the combination. In a further aspect, an effective amount of a further therapy is administered such as an effective amount of leucovorin.

The therapy that the patient is likely responsive to is a chemotherapy comprising, or alternatively consisting essentially of, or alternatively consisting of, administration of an effective amount of a pyrimidine based antimetabolite chemotherapy drug such as 5-fluorouracil and platinum based chemotherapy, or an equivalent of each thereof. Examples of a platinum based chemotherapy drug is oxaliplatin or an equivalent thereof. Equivalents of each are described supra. In a further aspect, the chemotherapy comprises the administration of an efficacy enhancing agent such as leucovorin or an equivalent thereof. FOLFOX is an example of a combination chemotherapy comprising administration of 5-fluorouracil, leucovorin, and oxaliplatin and is an example of a therapy for selected patients.

Patient samples can include a gastrointestinal or other noted tumor cell or tissue sample, or normal tissue such as peripheral blood lymphocytes. In one aspect, the suitable cell or tissue sample comprises a colorectal cancer cell or tissue sample.

Methods to identify the disclosed polymorphisms are known in the art, for example, ER-β polymorphism CA repeat at 3'UTR and A1730G (a/k/a G1730A) were described in Westberg et al. (2001) J. Clin. Endocrinol. Metab. 86:2562-2568 and Maguire et al. (2005) Breast Cancer Res. Treat. 94:145-152, respectively. The IL-8 T-251A polymorphism and CXCR2 polymorphism C379T were described in Zhang et al. (2005) Clin. Colorectal Cancer 5:124-134. Additional methods are known to Applicant and described, for example in U.S. Patent Publication Nos.: 2006/0115827 and 2006/0094012. Probes and primers are also disclosed in the experimental section below.

Diagnostic Methods

The invention further provides diagnostic methods, which are based, at least in part, on determination of the identity of the polymorphic region or expression level (or both in combination) of the polymorphism identified in Table 1, above.

For example, information obtained using the diagnostic assays described herein is useful for determining if a subject will respond to cancer treatment of a given type. Based on the prognostic information, a doctor can recommend a therapeutic protocol, useful for treating reducing the malignant mass or tumor in the patient or treat cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of point mutations or additional base pair repeats (as required for the ER-β polymorphism) can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (Maxam and Gilbert (1997) Proc. Natl. Acad Sci, USA 74:560) or Sanger (Sanger et al. (1977) Proc. Nat. Acad. Sci, 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249; Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci. USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polylmorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren, U. et al. Science 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996) Nucleic Acids Res. 24:3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen, D. et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C. et al. (1990) Genomics 8:684-692; Kuppuswamy, M. N. et al. (1991) Proc. Natl. Acad. Sci. (U.S.A.) 88:1143-1147; Prezant, T. R. et al. (1992) Hum. Mutat. 1:159-164; Ugozzoli, L. et al. (1992) GATA 9:107-112; Nyren, P. et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C. et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al., (1989) supra, at Chapter 18. The protein detection and isolation methods employed herein can also be such as those described in Harlow and Lane, (1988) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding of a primer, probe, polynucleotide, an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject is likely responsive to the therapy as described herein or has or is at risk of developing disease such as colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo, G. J. (1992) "PCR In Situ Hybridization: Protocols And Applications", Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S, and Kramer, F. R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis, L. G. (1998) Science 279:1228-9) as has the use of multiple beacons simultaneously (Marras, S. A. (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Patent No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the polymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley, S. O. et al. (1999) Nucleic Acids Res. 27:4830-4837.

In addition, this invention also provides a panel of genetic markers for determining whether a gastrointestinal cancer is likely responsive to a chemotherapy regime comprising administration of a pyrimidine based antimetabolite chemotherapy drug and a platinum based chemotherapy drug or an equivalent of each thereof, wherein the panel contains at least one, two, three or four of a group of primers and/or probes that identify a genetic marker from the group: CA repeats of the ER-β 3'UTR; ER-β A1730G SNP; IL-8 T-251A SNP; and CXCR2 C785T SNP alone or in combination with other probes or primers. In a particular aspect, the panel comprises probes and/or primes to (1 allele with <22 CA repeats) of the ER-β 3'UTR; (G/G or A/G) of the ER-β A1730G SNP; (A/A) for the IL-8 T-251A SNP; or (T/T or T/C) for the CXCR2 C785T SNP, alone or in combination with other probes or primers.

In one aspect, the panel contains the above identified probes or primers as wells as other, probes or primers. In a alternative aspect, the panel includes one or more of the above noted probes or primers and others. In a further aspect, the panel consist only of the above-noted probes or primers.

Primers or probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarray" and similar technologies are know in the art. Examples of such include, but are not limited to LabCard (ACLARA Bio Sciences Inc.); GeneChip (Affymetrix, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "Gene chips" or a "microarray" are also described in US Patent Publ. Nos.: 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers for genes of Table 1 are provided alone or in combination are prepared. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genotypes of the patient is then determined with the aid of the aforementioned apparatus and methods.

Nucleic Acids

In one aspect, the nucleic acid sequences of the gene's allelic variants, or portions thereof, can be the basis for probes or primers, e.g., in methods for determining the identity of the allelic variant of a gene identified in the experimental section below. Thus, they can be used in the methods of the invention to determine which therapy is most likely to treat an individual's cancer.

The methods of the invention can use nucleic acids isolated from vertebrates. In one aspect, the vertebrate nucleic acids are mammalian nucleic acids. In a further aspect, the nucleic acids used in the methods of the invention are human nucleic acids.

Primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in viva), or agents facilitating transport across the cell membrane. See, e.g., Letsinger et al. (1989) Proc. Natl. Acad. Sci. U.S.A. 86:6553-6556; Lemaitre et al. (1987) Proc. Natl. Acad. Sci. 84:648-652; and PCT Publication No. WO 88/09810, published Dec. 15, 1988), hybridization-triggered cleavage agents, (see, e.g., Krol et al. (1988) BioTechniques 6:958-976) or intercalating agents (see, e.g., Zon (1988) Pharm. Res. 5:539-549. To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods known in the art and described, e.g., in Sambrook et al. (1989) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

Methods of Treatment

The invention further provides methods of treating subjects having solid malignant tissue mass or tumor selected from rectal cancer, colorectal cancer, (including metastatic CRC), colon cancer, gastric cancer, lung cancer (including non-small cell lung cancer) and esophageal cancer. Without being bound by theory, Applicants intend that the methods are also useful to treat patients identified to likely to respond to the combination therapy when the patient is suffering from lung cancer, ovarian cancer, head and neck cancer or hepatocarcinoma as these cancers have been successfully treated with an effective amount of a pyrimidine based antimetabolite chemotherapy drug and a platinum based chemotherapy drug such as 5-FU and/or oxaliplatin and equivalents of each thereof.

In one embodiment, the method comprises (a) determining the identity of the allelic variant as identified herein; and (b) administering to the subject an effective amount of a compound or therapy (e.g., chemotherapy with 5-fluorouracil and oxaliplatin, or an equivalent of each thereof). This therapy can be combined with other suitable therapies or treatments as described above.

The chemotherapy comprises, or alternatively consists essentially of, or yet further consists of administration of a pyrimidine based antimetabolite chemotherapy drug and a platinum based chemotherapy drug, e.g., 5-fluorouracil and oxaliplatin or FOLFOX or equivalents thereof, in an amount effective to treat the cancer and by any suitable means and with any suitable formulation as a composition and therefore includes a carrier such as a pharmaceutically acceptable carrier. Accordingly, a formulation comprising the necessary chemotherapy or biological equivalent thereof is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The chemotherapeutic agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, fluorouracil/oxaliplatin, methotrexate-leucovorin, and the like.

Combinations of chemotherapies and molecular targeted therapies, biologic therapies, and radiation therapies are also well known to the art; including therapies such as trastuzumab plus paclitaxel, alone or in further combination with platinum compounds such as oxaliplatin, for certain breast cancers, and many other such regimens for other cancers; and the "Dublin regimen" 5-fluorouracil IV over 16 hours on days 1-5 and 75 mg/m$^2$ cisplatin IV or oxaliplatin over 8 hours on day 7, with repetition at 6 weeks, in combination with 40 Gy radiotherapy in 15 fractions over the first 3 weeks) and the "Michigan regimen" (fluorouracil plus cisplatin or oxaliplatin plus vinblastine plus radiotherapy), both for esophageal cancer, and many other such regimens for other cancers, including colorectal cancer.

An "effective amount" is an amount sufficient to effect beneficial or desired results. An effective amount can be administered in one or more administrations, applications or dosages.

The invention provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

When an antibody is administered, the antibody or equivalent thereof is prepared to a concentration includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Chemotherapeutic formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject® NovoPen®, B-D®Pen, AutoPen®, and OptiPen®, GenotropinPen®, Genotronorm Pent, Humatro Pen®, Reco-Pen®, Roferon Pent, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a chemotherapeutic agent of the invention, e.g., encapsulation in liposomes, microparticles, microcapsules, expression by recombinant cells, receptor-mediated endocytosis. See e.g., Wu and Wu (1987) J. Biol. Chem. 262:4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the invention locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a medicament comprising an effective amount of a chemotherapeutic as described herein for treatment of a human cancer patient having one or more predictive polymorphisms or genetic markers as identified in Table 1 or the experimental examples.

Kits

As set forth herein, the invention provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest. Accordingly, the invention provides kits for performing these methods as well as instructions for carrying out the methods of this invention such as collecting tissue and/or performing the screen, and/or analyzing the results, and/or administration of an effective amount of the 5-FU/oxaliplatin or equivalents of each thereof, alone or in combination with other suitable chemotherapy or biological therapy.

In an embodiment, the invention provides a kit for determining whether a subject is likely responsive to cancer treatment or alternatively one of various treatment options. The kits contain one of more of the compositions described above and instructions for use. As an example only, the invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard, T. (1986) AN INTRODUCTION TO RADIOIMMUNOASSAY AND RELATED TECHNIQUES Elsevier Science Publishers, Amsterdam, The Netherlands; Bullock, G. R. et al., TECHNIQUES IN IMMUNOCYTOCHEMISTRY Academic Press, Orlando, Fla. Vol. 1 (1982), Vol. 2 (1983), Vol. 3 (1985); Tijssen, P. (1985) PRACTICE AND THEORY OF IMMUNOASSAYS: LABORATORY TECHNIQUES IN BIOCHEMISTRY AND MOLECULAR BIOLOGY, Elsevier Science Publishers, Amsterdam, The Netherlands.

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.

Other Uses for the Nucleic Acids of the Invention

The identification of the allele of the gene of interest can also be useful for identifying an individual among other individuals from the same species. For example, DNA sequences can be used as a fingerprint for detection of different individuals within the same species. Thompson, J. S, and Thompson, eds., (1991) GENETICS IN MEDICINE, W B Saunders Co., Philadelphia, Pa. This is useful, e.g., in forensic studies.

The invention now being generally described, it will be more readily understood by reference to the following examples which are included merely for purposes of illustration of certain aspects and embodiments of the present invention, and are not intended to limit the invention.

EXPERIMENTAL EXAMPLES

Experiment No. 1

For the purpose of illustration only, peripheral blood sample can be collected from each patient, and genomic DNA can be extracted from white blood cells using the QiaAmp kit (Qiagen, Valencia, Calif.).

Background Many factors contribute to the progression of colorectal cancer and to chemoresistance. Two factors that have recently gained attention are angiogenesis and sex hormones. Interleukin-8 and its receptors play a critical role in angiogenesis, and polymorphisms in these genes have previously been reported to predict clinical outcome and resistance to therapy in a variety of cancer types. In addition, gender and the subsequent varied levels of sex hormones between males and females may also have an impact on colorectal cancer progression. Sex hormones such as estrogen exert their effects on the cell by binding to steroid receptors such as estrogen receptor beta (ER-β). It is known that ER-β is predominantly expressed in the colon, and that differential expression of this gene is predictive of clinical outcome. Therefore, functional polymorphisms within ER-β, IL-8, and the IL-8 receptors are useful as molecular markers for predicting clinical outcome in colorectal cancer patients.

Methods 173 patients were enrolled in this phase II study. 152 patients were evaluable for genotyping and statistical analysis. There were 74 females and 78 males, and median age was 60 (range 25-87). The dose of oxaliplatin was 130 mg/m$^2$ every 3 weeks and 5-FU was 200 mg/m$^2$/day CI for 10 weeks followed by 2 weeks rest. Polymorphisms in estrogen receptor beta, IL-8, and CXCR2 (IL-8 receptor) were tested by PCR.

Results Median follow-up was 18.6 months, response rate 19%, median time to tumor progression 4.2 months and median survival 10.3 months. IL-8 T-251A polymorphism was predictive of time to tumor progression (p=0.04, log-rank test). ER-β CA repeat polymorphism was predictive of tumor response as well as time to tumor progression (p=0.015, p=0.012, respectively). ER-β A1730G SNP was also predictive of time to tumor progression (p=0.03). Polymorphism in CXCR2 was predictive of tumor response (p=0.034).

Conclusions These results show that polymorphisms within IL-8, CXCR2, and ER-13 affect the progression of colorectal cancer and subsequent clinical outcome. These results highlight the importance of angiogenesis and hormone levels in colorectal cancer.

Experiment No. 2

Experiment No. 2 is an extension of the study reported in Experiment No. 1.

Background The role of angiogenesis in cancer progression and chemoresistance has been well established. Interleukin-8 (IL-8) and its receptors play a critical role in angiogenesis, and polymorphisms in these genes have previously been reported to predict clinical outcome and resistance to therapy in a variety of cancer types. IL-8 acts through its receptors CXCR1 and CXCR2, and affects such downstream processes as apoptosis inhibition, chemotaxis, protease activation, proliferation, and angiogenesis. IL-8 is also associated with oxaliplatin sensitivity. There are common polymorphic variants within IL-8 and its receptors that may affect the function of these genes.

Recently, sex boil cones have gained significant attention in their role in resistance to colorectal cancer. Gender and the subsequent varied levels of sex hormones between males and females may further impact colorectal cancer progression. Sex hormones such as estrogen exert their effects on the cell by binding to steroid receptors such as estrogen receptor beta (ER-β). It is known that ER-β is predominantly expressed in the colon, and that differential expression of this gene is predictive of clinical outcome in colorectal cancer.

In this study, functional polymorphisms within ER-β, IL-8, and the IL-8 receptors were examined to determine their role as potential molecular markers for predicting clinical outcome in metastatic colorectal cancer patients treated with 5-FU/oxaliplatin.

Methods Subjects included in this study were enrolled in the 3C-01-7 clinical trial. The study was a phase II study of oxaliplatin in combination with continuous infusion 5-FU in patients with colorectal cancer refractory to 5-FU/CPT-11 based chemotherapy. This study was conducted at the Norris Comprehensive Cancer Center and was approved by the Institutional Review Board of the University of Southern California (USC, CA, USA) for Medical Sciences. Patients were accrued from September 2001 to August 2004. A total of 173 patients were accrued to this trial. All patients signed informed consent prior to entering this study. Tumor biopsy from time of diagnosis and peripheral blood were collected for each patient. All patients were at least 18 years of age, had SWOG performance status ≦2, and had stage 1V metastatic colorectal cancer. The dose of oxaliplatin administered was 130 mg/m2 every 3 weeks and 5-FU was 200 mg/m2/day CI for 10 weeks followed by 2 weeks rest. Baseline evaluations were conducted within 1 week prior to administration of study drug. Scans and x-rays were conducted ≦4 weeks prior to the start of therapy. The Response Evaluation Criteria In Solid Tumors (RECIST) and CTC 2.0 toxicity criteria were used. Tumor response was evaluated every six weeks and toxicity was evaluated every 3 weeks or as needed.

PCR Single nucleotide polymorphisms in ER-β, IL-8, and CXCR2 (IL-8 receptor) were tested by PCR and restriction fragment length polymorphism analysis (RFLP). The ER-β, (CA)n repeat polymorphism was determined using 33P-γATP end-labeled technique. The primer sequences used in these studies were as follows: IL-8 T-251A forward -5'-TTGTTCTAACACCTGCCACTCT-3' (SEQ ID NO. 1), reverse -5'-GGCAAACCTGAGTCATCACA-3' (SEQ ID NO. 2); CXCR2 forward -5'-CATCTTTGCTGTCGTC-CTCA-3' (SEQ ID NO. 3), reverse -5'-CTCACAGGTCTC-CTGGATCA-3' (SEQ ID NO. 4); ER-β (CA)n repeat polymorphism forward -5'GGTAAACCATGGTCTGTACC-3' (SEQ ID NO. 5) and reverse 5'-AACAAAATGTTGAAT-GAGTGGG-3' (SEQ ID NO. 6).

Results and Conclusion There were 74 females and 78 males, and median age was 60 years (range 25-87). There were 105 Caucasian, 24 Asian, 18 Hispanic, and 5 African American patients. Ninety-one patients had primary tumor localized to the colon, 38 to the rectosigmoid junction, 22 to the rectum, and 1 to the appendix. The response rate was 19% (complete response or partial response; 95% CI: 13%-26%). One patient (1%) had a complete response, 27 patients (18%) had partial response, 66 patients (44%) had stable disease, 55 patients (37%) had progressive disease, and 3 patients could not be evaluated for response. Median overall survival was 10.3 months, and median progression free survival was 4.2 months.

Figure 2:
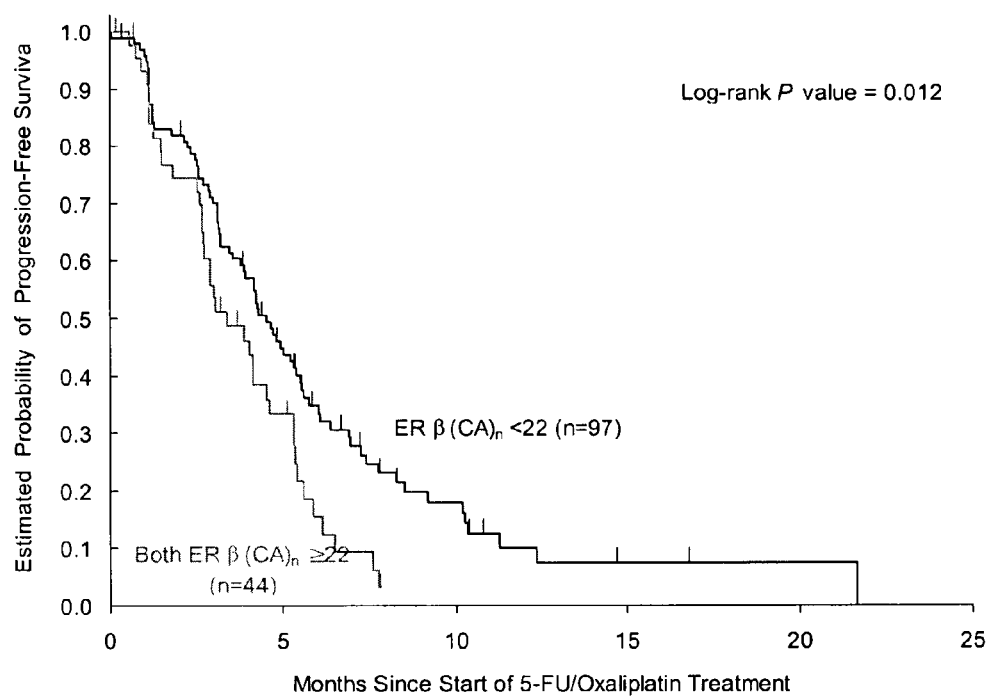
FIG. 2 graphically shows that patients possessing at least one allele with less than 22 CA repeats in the ER-β gene are more likely responsive to disclosed therapy than those having both alleles with more than 22 CA repeats. It shows that progression free survival is associated with the number of CA repeats in the ER-β gene.
Figure 3:
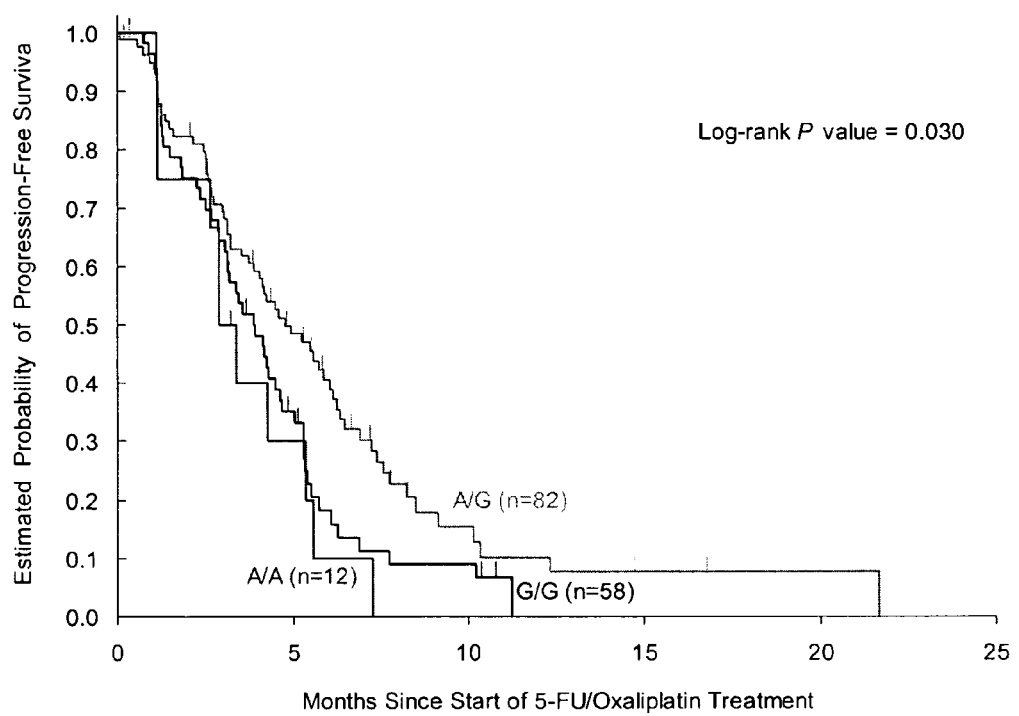
FIG. 3 graphically shows that patients possessing the A/G or G/G alleles for the ER-β gene are more likely to show responsiveness to the therapy than those possessing the A/A genotype. It also shows that progression-free survival is associated with the ER-β polymorphism.

IL-8 T-251A polymorphism was predictive of time to tumor progression (p=0.04, log-rank test) (FIG. 1). ER-β CA repeat polymorphism was predictive of tumor response as well as time to tumor progression (p=0.015, p=0.012, respectively) (FIG. 2 and Table 2). ER-β A1730G SNP was also predictive of time to tumor progression (p=0.03) (FIG. 3.). Polymorphism in CXCR2 was predictive of tumor response (p=0.034) (Table 2).

Table 2 and FIGS. 1 through 3 graphically show the results of this study. For the IL-8 and CXCR2 polymorphisms, patients bearing polymorphisms that have previously been shown to increased IL-8 expression (T/A or T/T of the T-251A SNP) demonstrate decreased TTP. In this study, it was found that patients that were homozygous for the C allele of the C+785T SNP of the CXCR2 gene demonstrated decreased tumor response when compared to patients that were homozygous (T/T) or heterozygous for this allele.

Thus, this data implicates the IL-8/CXCR2 pathway as a mediator of colon cancer progression and response following treatment with 5-FU/oxaliplatin.

For the ER-β polymorphisms, the ER-β (CA)n>22 repeat polymorphism within the 3'UTR was associated with decreased response and decreased time to tumor progression (TTP), while the ER-β (CA)n<22 repeat polymorphism was associated with increased response (TR) and increased time to tumor progression (TTP).

Patients bearing any G allele of the A1730G ER-β polymorphism demonstrated increased response and increased TTP, while the patients that were heterozygous for the A allele demonstrated decreased response and decreased TTP.

This data supports the role of ER-β polymorphisms as prognostic markers in metastatic colon cancer.

TABLE 2

Polymorphisms and Response to 5-FU/Oxaliplatin

| | N | CR + PR | SD | PD | P* |
|---|---|---|---|---|---|
| ER-β | | | | | 0.66 |
| G/G | 58 | 15 (27%) | 17 (30%) | 24 (43%) | |
| A/G | 82 | 12 (15%) | 44 (54%) | 25 (31%) | |
| A/A | 12 | 1 (8%) | 5 (42%) | 6 (50%) | |
| ER-β 22 | | | | | 0.015 |
| Any < 22 | 94 | 21 (22%) | 44 (47%) | 29 (31%) | |
| Both[3] 22 | 44 | 4 (9%) | 18 (41%) | 22 (50%) | |
| IL-8 | | | | | 0.34 |
| T/T | 46 | 10 (22%) | 23 (50%) | 13 (28%) | |
| A/T | 76 | 13 (18%) | 29 (40%) | 31 (42%) | |
| A/A | 20 | 5 (25%) | 7 (35%) | 8 (40%) | |
| CXCR2 | | | | | 0.034 |
| C/C | 42 | 1 (2%) | 20 (49%) | 20 (49%) | |
| C/T | 59 | 18 (32%) | 24 (42%) | 15 (26%) | |
| T/T | 36 | 6 (17%) | 19 (53%) | 11 (31%) | |

*P values were based on the exact Jonckheere-Terpstra test for response, and Fisher's exact test for toxicity.
†PR: Partial Response, SD: Stable Disease, PD: Progressive Disease It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for determining whether a human gastrointestinal cancer patient is likely or not likely responsive to a therapy comprising administration of a pyrimidine based antimetabolite chemotherapy drug and a platinum based chemotherapy drug, comprising screening a suitable cell or tissue sample isolated from the patient for the genetic polymorphism of:

IL-8 T-251A SNP and determining that the patient is likely responsive to the therapy if the genotype A/A at the IL-8 T-251A SNP is present in the sample, or the patient is not likely responsive to the therapy if the genotype is not present in the sample.

2. The method of claim 1, wherein the gastrointestinal cancer is a metastatic or non-metastatic cancer selected from the group consisting of rectal cancer, colorectal cancer, colon cancer, gastric cancer, and esophageal cancer.

3. The method of claim 1, wherein the gastrointestinal cancer is colorectal cancer.

4. The method of claim 3, wherein the colorectal cancer is refractory to 5-fluorouracil and irinotecan based chemotherapy.

5. The method of claim 3, wherein the suitable cell or tissue sample comprises a colorectal cancer cell or tissue sample.

6. The method of claim 1, wherein the gastrointestinal cancer is metastatic colorectal cancer.

7. The method of claim 1, wherein the pyrimidine based antimetabolite chemotherapy drug is a 5-fluorouracil or an equivalent thereof.

8. The method of claim 1, wherein the platinum based chemotherapy drug is oxaliplatin or an equivalent thereof.

9. The method of claim 1, further comprising the administration of an efficacy enhancing agent to the patient.

10. The method of claim 9, wherein the efficacy enhancing agent is leucovorin or an equivalent thereof.

11. The method of claim 1, wherein the therapy comprises the administration of a 5-fluorouracil, leucovorin, and oxaliplatin (FOLFOX).

12. The method of claim 1, wherein the suitable cell or tissue sample comprises a tumor cell or tissue sample.

13. The method of claim 1, wherein the suitable cell or tissue sample comprises peripheral blood lymphocytes.

14. A method for treating a human gastrointestinal cancer patient comprising administering to a human gastrointestinal cancer patient a therapy comprising an effective amount of a pyrimidine based antimetabolite chemotherapy drug and a platinum based chemotherapy drug, wherein the patient is selected for having the genotype of A/A at IL-8 T-251A SNP.

15. The method of claim 14, wherein the gastrointestinal cancer is a metastatic or non-metastatic cancer selected from the group consisting of rectal cancer, colorectal cancer, colon cancer, gastric cancer, and esophageal cancer.

16. The method of claim 14, wherein the gastrointestinal cancer is colorectal cancer.

17. The method of claim 14, wherein the gastrointestinal cancer is metastatic colorectal cancer.

18. The method of claim 16, wherein the colorectal cancer is refractory to 5-fluorouracil and irinotecan based chemotherapy.

19. The method of claim 14, wherein the pyrimidine based antimetabolite chemotherapy drug is a 5-fluorouracil or an equivalent thereof.

20. The method of claim 14, wherein the platinum based chemotherapy drug is oxaliplatin or an equivalent thereof.

21. The method of claim 14, further comprising the administration of an efficacy enhancing agent to the patient.

22. The method of claim 21, wherein the efficacy enhancing agent is leucovorin or an equivalent thereof.

23. The method of claim 14, wherein the therapy comprises a 5-fluorouracil, leucovorin, and oxaliplatin (FOLFOX).

24. The method of claim 14, further comprising screening a suitable cell or tissue sample isolated from the patient for at least one genetic polymorphism of: the CA repeats of the ER-β 3'UTR, the ER-β A1730G SNP, the IL-8 T-251A SNP, or the CXCR2 C785T SNP.

25. The method of claim 24, wherein the screening comprises a method selected from sequencing, PCR, allele specific hybridization, denaturing gradient gel electrophoresis (DGGE), selective oligonucleotide hybridization, selective amplification, or selective primer extension, oligonucleotide ligation assay (OLA), Genetic Bit Analysis, or restriction fragment length polymorphism analysis (RFLP).

* * * * *